June 11, 1946. R. L. BYRUM Plant Pat. 694
ROSE PLANT
Filed Oct. 24, 1945
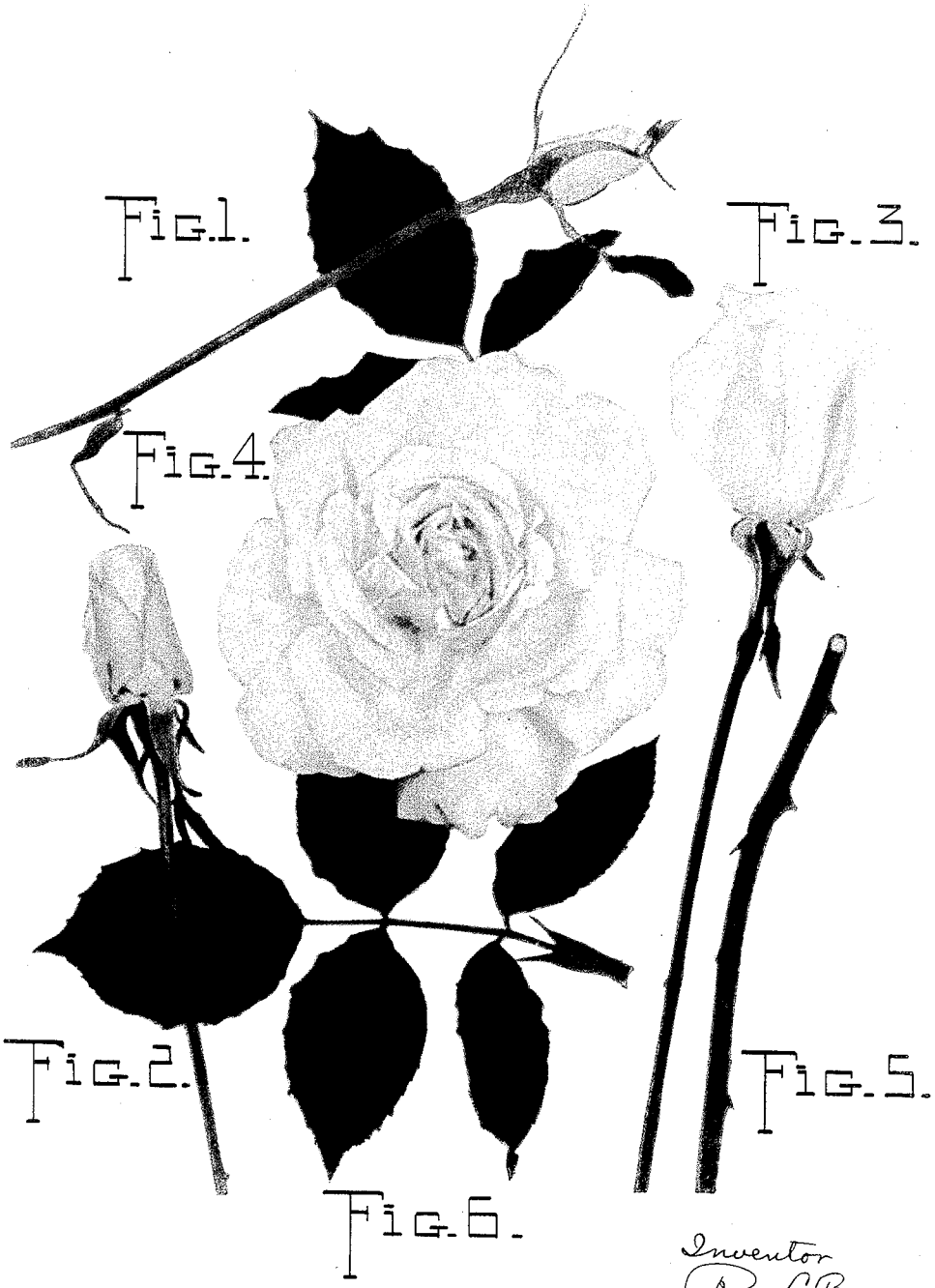
Inventor
Roy L. Byrum
By Robb & Robb
attorneys Patented June 11, 1946

Plant Pat. 694

UNITED STATES PATENT OFFICE

694

ROSE PLANT

Roy L. Byrum, Richmond, Ind., assignor to Joseph H. Hill Company, Richmond, Ind., a corporation of Indiana Application October 24, 1945, Serial No. 624,229

1 Claim. (Cl. 47—61)

The present discovery relates to a new and distinct variety of rose plant, particularly suitable as a greenhouse forcing variety, originating as a sport of "Better Times" (Pl. Patent #23).

This sport was discovered by me while budding eyes on "Better Times" plants, and was recognized at once as wholly distinguishable from its parent variety.

By asexual methods of reproduction of the new variety and customary tests, it was determined that this sport followed most closely the growth and habits of the Briarcliff group, of which "Better Times" and "Peter's Briarcliff" are typically representative. In color impression, it most nearly resembles the variety "Vanity Fair" (Pl. Patent #583), and thus comparison with the latter to show the distinctiveness of the sport is appropriate.

In the first place, the present variety has a stiff neck whereas that of "Vanity Fair" is very bending. "Vanity Fair" has more thorns and its buds are not as pointed as found in this sport. The primary distinguishing characteristic is the scalloped edges of the petals.

In the drawing:

Figure 1 is a view showing the bud as calyx breaks;

Figure 2 is a view of the bud as first petal opens;

Figure 3 shows the bloom at the half-blown stage;

Figure 4 shows the full blown flower;

Figure 5 is a view of a section of a branch disclosing the arrangement, form and color of the thorns; and Figure 6 depicts a specimen of the foliage and stipules.

Asexual reproduction of this new variety shows the foregoing characteristics come true to form and are established.

The following is a detailed description of the new variety, color terminology being in accord with Ridgway's Color Standard, except where otherwise indicated to have ordinary dictionary significance:

Type: Tall; bush; greenhouse; sport; for cut flowers.

Class: Hybrid, tea.

Breeding: Sport.

*Parent.*—"Better Times."

Propagation: Holds its distinguishing characteristics through succeeding propagations by cutting, grafting, and budding. Layering not yet tried.

Locality where grown: Richmond, Indiana.

Flowers borne: Singly on strong, medium stems.

Quantity of bloom: Abundant, in greenhouse.

Continuity: Continuous, in greenhouse.

Fragrance: Strong; tea.

Bud:

*Peduncle.*—Long; heavy; stiff; Green; almost smooth; few Green hairs.

*Before calyx breaks.*—*Size*—medium. *Form*—long; pointed, with a conspicuous neck; with foliaceous appendages on the surface of the bud; with slender bristle-like foliaceous parts extending beyond the tip of the bud equal to ¾ or more of its length.

*As calyx breaks.*—*Color*—Begonia Rose, Plate 1.

*As first petal opens.*—*Size*—medium. *Form*—long; pointed. *Color*—outside: Eosine Pink, Plate 1, shaded with Begonia Rose, Plate 1; inside: Eosine Pink, Plate 1, shaded with Begonia Rose, Plate 1.

*Opening.*—Opens up well.

Bloom:

*Size when fully open.*—Very large; 4 to 5 inches.

*Petalage.*—Double; from 25 to 35 petals, arranged irregularly.

*Form.*—Very high center; petals remaining at first tightly rolled outward, becoming later, at maturity, loosely rolled outward.

Petals: Thick; leathery; with inside and outside satiny.

*Shape.*—Outside—obovate; scalloped. Intermediate—obovate; scalloped. Inside—obovate; scalloped; irregular.

This description of a newly opened flower was made from a rose grown in a greenhouse in the month of April, at Richmond, Indiana:

*Color—Outside petal*—outside surface: Hermosa Pink, Plate 1; inside surface: Hermosa Pink, Plate 1, pencilled with Eosine Pink, Plate 1. *Intermediate petal*—outside surface: Hermosa Pink, Plate 1, shaded with Eosine Pink, Plate 1; inside surface: Hermosa Pink, Plate 1, shaded with Eosine Pink, Plate 1. *Inner petal*—outside surface: Hermosa Pink, Plate 1, shaded with Eosine Pink, Plate 1; inside surface: Hermosa Pink, Plate 1, shaded with Eosine Pink, Plate 1.

This description was made from a rose that was open for three days in the month of March, at Richmond, Indiana:

*Color.—Outside petal*—outside surface: between Hermosa Pink, Plate 1, and White; inside surface: between Hermosa Pink, Plate 1, and White. *Inside petal*—outside surface: Hermosa Pink, Plate 1; inside surface: Hermosa Pink, Plate 1.

*General color effect.*—Newly opened flower—Hermosa Pink, Plate 1. Three days open—between Hermosa Pink, Plate 1, and White.

*Behavior.*—Persistent; fading slightly.

*Flower longevity.*—Cut roses grown in greenhouse kept at living room temperatures—4 to 5 days in March.

*Reproductive organs*

Stamens: Many; arranged regularly about pistils.
Filaments: Long; Yellow; most with anthers.
Anthers: Medium number; large; Yellow; all open at once.
Pollen: Abundant; Gold.
Pistils: Very many.
Styles: Uneven; medium long; medium heavy; bunched.
Stigma: White.
Ovaries: Some protruding from calyx.
Sepals: Permanent; long; spear-shaped, with a few curled.
Hips: None developed as yet.
Seeds: None developed as yet.

*Plant*

Foliage:

*Leaves*—Compound of 5; very abundant; large; leathery.

*Leaflets.*—Ovoid, with apex acute; base round; margin simply serrate.

*Color.—Mature*—upper surface: very Dark Green; under surface: moderately Light Green. *Young*—upper surface: Dark Red; under surface: Light Red.

*Rachis.*—Heavy; upper side, grooved; under side, smooth.

*Stipules.*—Moderately short; medium width; with moderately short points turning out at an angle of less than 90°.

*Disease.*—Resistant to mildew and blackspot.

Growth:

*Habit.*—Bushy; upright; much branched.

*Growth.*—Free; vigorous.

*Canes.*—Heavy.

*Main stems.*—Gray Green. *Thorns*—few; short; hooked downward with short narrow base. *Prickles and hairs*—None.

*Branches.*—Bright Green. *Thorns*—few; short; hooked downward with short narrow base. *Prickles and hairs*—none.

*New shoots.*—Dull Red. *Thorns*—few; short; hooked downward with short narrow base. *Prickles and hairs*—none.

I claim:

A new and distinct variety of rose plant, characterized as to novelty by the color of the blooms, stiffness of the neck bearing said blooms, pointed form of buds, lesser quantity of thorns as compared with the variety "Vanity Fair" which it most nearly resembles, and scalloped edges of the petals, substantially as shown and described.

ROY L. BYRUM.